United States Patent [19]

White

[11] 4,242,759
[45] Jan. 6, 1981

[54] M.C.P. JOINT REPLACEMENT

[75] Inventor: Robert C. White, Beamsville, Canada

[73] Assignee: Ontario Research Foundation, Mississauga, Canada

[21] Appl. No.: 19,517

[22] Filed: Mar. 12, 1979

[51] Int. Cl.³ .............................................. A61F 1/03
[52] U.S. Cl. ..................................... 3/1.91; 128/92 C
[58] Field of Search .............................. 3/1.91, 1.911; 128/92 C

[56] References Cited

U.S. PATENT DOCUMENTS

| | | | |
|---|---|---|---|
| 3,506,982 | 4/1970 | Steffee | 3/1.91 |
| 3,878,566 | 4/1975 | Bechtol | 128/92 C X |
| 3,946,445 | 3/1976 | Bentley et al. | 3/1.91 |
| 3,991,425 | 11/1976 | Martin et al. | 3/1.91 |
| 4,038,704 | 8/1977 | Ring | 3/1.91 |
| 4,069,518 | 1/1978 | Groth, Jr. et al. | 3/1.91 |
| 4,156,944 | 6/1979 | Schreiber et al. | 3/1.91 |

FOREIGN PATENT DOCUMENTS

| | | | |
|---|---|---|---|
| 1333412 | 10/1973 | United Kingdom | 3/1.911 |
| 1520162 | 8/1978 | United Kingdom | 3/1.911 |

Primary Examiner—Clifford D. Crowder
Attorney, Agent, or Firm—Sim & McBurney

[57] ABSTRACT

There is provided a metacarpal-phalangeal joint replacement having two members, one for insertion into each of the respective bones in the joint. Each member defines a tail and a head, and the two heads are adapted to fit with each other in such a way that when the finger is extended, the joint and thus the finger have a limited degree of lateral freedom to swing from side to side, whereas when the finger is flexed, this lateral freedom is considerably restricted. This variation is brought about by making the face of one head generally protuberant, and the face of the other head generally recessed or channeled. The "match" in contour between the two faces thus varies during the pivoting of the one member with respect to the other, between a substantially complementary fit when the finger is flexed, to a "loose" or "wobble" fit when the finger is extended.

5 Claims, 11 Drawing Figures

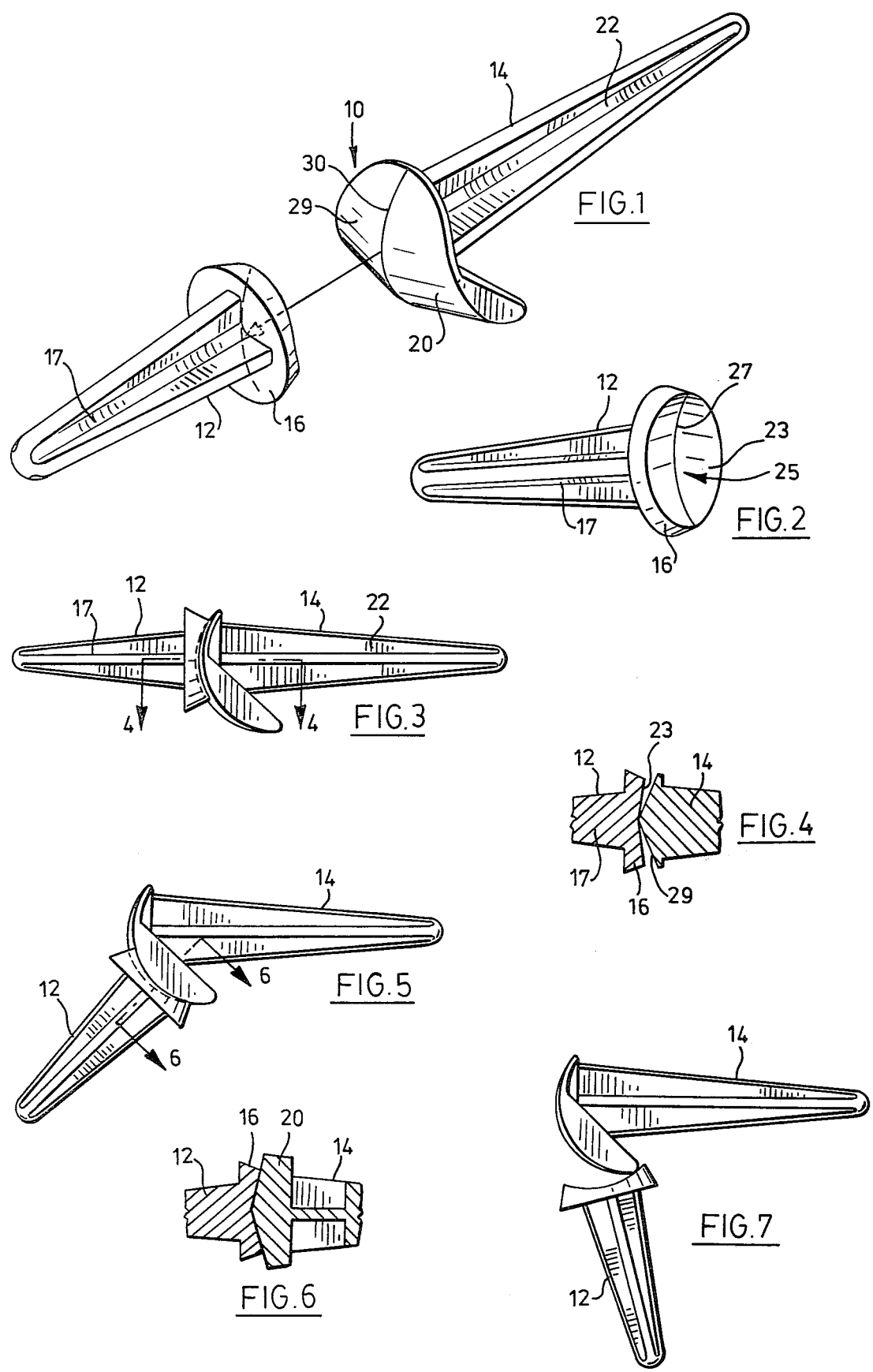

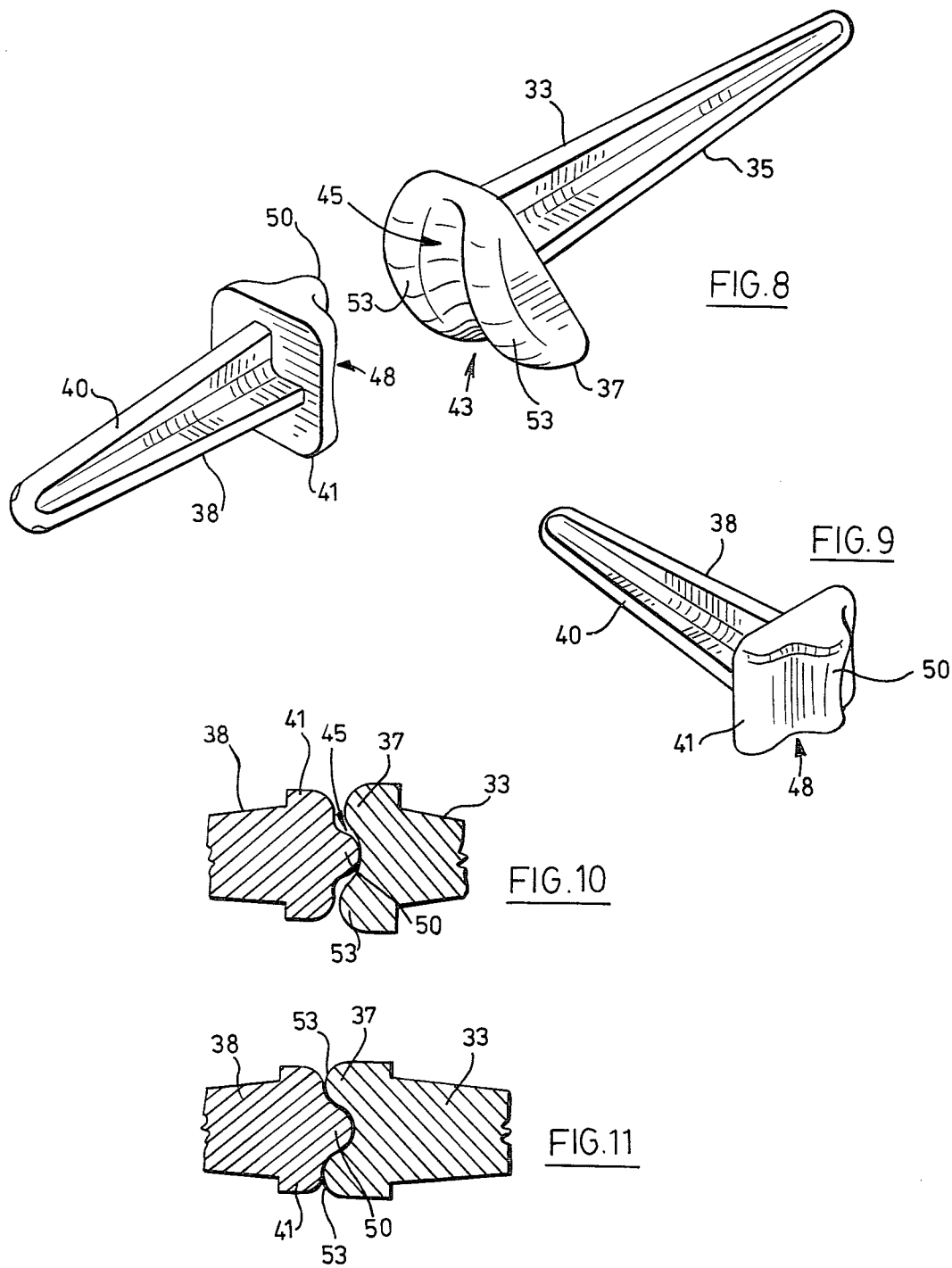

M.C.P. JOINT REPLACEMENT

This invention relates generally to the field of surgical prosthetic devices used in medicine, and has to do particularly with what is called a joint replacement. Specifically, this invention has to do with the surgical correction of joints in the hand, in particular the metacarpal-phalangeal joint.

The structure of the normal human hand is such that when the fingers are extended, i.e. lie substantially in a plane parallel with the palm of the hand, each finger has a certain degree of lateral flexibility about its joint with the palm, and can be moved without discomfort through an angle of at least 30° to 40°. The joint undergoing flexure during such movement is that between the proximal phalanx of the finger and the metacarpal bone within the palm of the hand.

When the fingers of the hand are flexed through about 90° with respect to the palm (so that the major knuckle is a right-angle), the fingers lose a large part of the lateral freedom which they have when extended. This change in the degree of lateral freedom arises because of the way the metacarpal and phalangeal bones fit together, and due to the various ligaments which hold the bones in the correct association.

Since the aim of all medical prostheses is to reconstruct a bone or joint to be as close as possible in function to a similar healthy joint, it is an aspect of this invention to provide a metacarpal-phalangeal joint replacement which allows the finger a substantial degree of lateral flexural freedom when extended, and a more limited degree of such lateral freedom when flexed at right-angles to the palm.

Accordingly, this invention provides a joint replacement comprising:

a first member having a head portion an an elongated tail portion, the latter adapted for insertion into one bone of a joint, a second member having a head portion and an elongated tail portion, the latter adapted for insertion into another bone of the joint, the head of said first member defining a female contact face remote from the tail portion of the first member, said face being centrally indented to define a curved trough with the curve lying in a plane containing the tail portion of the first member, the head of said second member defining a male contact face remote from the tail portion of the second member, said male face being centrally protuberant to define a curved ridge with the curve lying in a plane containing the tail portion of the second member, the trough and the ridge being so shaped that, when the two members are in face-to-face contact in a first angular portion, the ridge and trough are substantially complementary with each other in the area of contact, such that lateral articulation the the tail portions in a plane normal to the planes of the ridge and trough is restrained, and when the two members are in face-to-face contact in a second angular position the respective contacting areas of the ridge and trough are non-complementary and such that the trough allows the ridge and its tail portion to articulate laterally in said plane normal to the ridge and trough planes the profile of the trough being substantially constant, and the profile of the ridge changing smoothly around the curve thereof from more protuberant to less protuberant.

Two embodiments of this invention are illustrated in the accompanying drawings, in which like numerals denote like parts throughout the several views, and in which:

FIG. 1 is a perspective view of a first embodiment of this invention;

FIG. 2 is a perspective view of one component shown in FIG. 1, seen from a different angle;

FIG. 3 is an elevational view of the FIG. 1 components in contact;

FIG. 4 is a sectional view taken at the line 4—4 in FIG. 3;

FIG. 5 is an elevational view of the FIG. 1 components in contact at a different angle from that shown in FIG. 3;

FIG. 6 is a sectional view taken along the line 6—6 in FIG. 5;

FIG. 7 is a view similar to FIG. 5, showing the components at the end of the flexural movement;

FIG. 8 is a perspective view of the components of a second embodiment of this invention;

FIG. 9 is a perspective view of one of the components of FIG. 8, from a different angle;

FIG. 10 is a sectional view through the FIG. 8 components in contact, when the latter are in a first orientation with respect to each other; and FIG. 11 is a sectional view through the FIG. 8 components in another angular relation.

Attention is first directed to FIG. 1 in which a joint replacement generally shown by the numeral 10 is seen to include a first member 12 and a second member 14. The first member has a head 16 and an elongated tail portion 17, the latter being adapted for insertion into one of the bones of the phalangeal-metacarpal joint of the hand. In the construction illustrated, the tail portion 17 would be adapted for insertion into the proximal phalanx of the respective finger.

The second member 14 also has a head portion 20 and an elongated tail portion 22, the latter being adapted for insertion into the other bone of the joint, in this case the metacarpal bone.

The head 16 of the first member 12 defines a female contact face 23 remote from the tail portion 17 of the first member 12. As can be seen in FIG. 2, the contact face 23 is centrally indented to define a curved trough 25 with the curve of the trough lying in a plane which contains the tail portion of the first member 12. More specifically, the profile of the trough 25 is constant, and is that of an obtuse-angled V as can be clearly seen in the sectional view of FIG. 4. In the embodiment illustrated, the profile of the trough is substantially constant along the apex line 27 which defines the centre point of the trough.

The line 27 thus is a smooth curve which lies in a plane extending back through what is substantially the centre of the tail portion 17.

Geometrically speaking, it may be considered that the face 23 of the head portion 16 of the first member 12 has the shape of a contiguous location on two identical right circular cones which are placed base to base. In more general terms, if one were to take two typical frusto-conical coffee cups and place them with their open ends matching and touching each other, then any small region along the joining line between the two coffee cups would have exactly the same geometrical shape as the face 23 in FIG. 2. The line 27 in FIG. 2 thus corresponds to the joining location between the rims of the two coffee cups.

The head 20 of the second member 14 defines a male contact face 29 remote from the tail portion 22 of the second member 14. The male face 29 is centrally protuberant to define a curved ridge whose curve lies in a plane containing the tail portion of the second member 14. More specifically, as can be seen in FIG. 1, the profile of the ridge on the face 29 is an inverted V-shape throughout. However, as can be seen by comparing FIGS. 4 and 6 (taken at different locations along the ridge line 30 of the face 29), the angle of the inverted V on the face 29 changes. More specifically, the angle defined by the V merges smoothly from a shape complementary with the trough defined by the member 12, as can be seen in FIG. 6, to a shape in which the angle of the V on face 29 is smaller than the angle on the face 23. In FIG. 4, it can be seen that both of the V shapes have obtuse angles, but that the V shape on the member 14 has a smaller angle than that on member 12.

Still more particularly, the location where the two V profiles do not match, i.e. where the V profile on the second member 14 is smaller in angle than the V profile on the first memer 12, corresponds to the FIG. 3 relationship between the two members, in which the tail portions 17 and 22 are approximately aligned and extend away from each other. Thus, the sharpest angle on the face 29 occurs in the upper portion as viewed in FIG. 3. The least angle of the V profile on the ace 29, i.e. the one which is complementary to the V shaped trough on the face 23, occurs down around the bottom of the face 20, to which the section of FIG. 6 corresponds. In this position, as seen in FIG. 5, the finger would be flexed through a given angle with respect to the metacarpal bone.

As can be appreciated, when the finger is extended parallel to the palm the relationship of FIG. 4 would occur, and due to the difference in the angles of the V-profiles, the finger would be allowed to articulate laterally (i.e. toward the other fingers), while the two V profiles coincided at their vertices. Conversely, with the finger flexed down so that it forms an angle with respect to the palm, the two V-profiles change to the point where they become complementary, and this complementary fit greatly restricts or prohibits lateral movement of the finger in that condition.

As can be particularly well seen in FIGS. 1, 3 and 5, the ridge on face 29 is substantially longer than the trough on the face 23, to allow the latter to slide down around the former. Thus, the two members act somewhat like portions of a ball socket, whose centre is approximately at the centre of curvature of the line 30 defining the vertex of the V profile on face 29.

FIG. 7 shows the two members in the maximum flexural position. As can be seen, the member 12 is pivoting away from the member 14 where their faces would ordinarily meet, and since the finger will be tied to the metacarpal by the usual ligaments, such a position will be very difficult to accomplish, as it is in the normal healthy hand. This restraint is due to the pulling or stretching of the ligaments that would occur in the FIG. 7 position.

In order to allow the face 29 of the second member 14 to define a V-shaped protuberance of which the apex angle varies from a smaller value in the upper part as seen in FIG. 4, to a larger value in the lower or under portion as seen in FIG. 6, the two flanks of the surface on either side of the curved ridge line 30 can again be compared to a juxtaposition of coffee cups, but in the case of the surface 29, the open ends of the coffee cups would have to be truncated along a somewhat oblique angle (i.e. so that they would no longer be right circular cones), and the coffee cups would then be placed mouth to mouth in such a way that the base location closest to the theoretical peak of one cup were aligned with the base location closest to the theoretical peak of the other. This would produce a joining location in which the angle between the surfaces would vary from a maximum at the base location closest to the theoretical peaks, to a minimum at the base location furthest from the theoretical peaks.

Attention is now directed to FIGS. 8-11, for a description of the second embodiment of this invention.

In FIG. 8, a first member 33 has a tail portion 35 and a head portion 37. A second member 38 has a tail portion 40 and a head portion 41.

The head portion 37 of the first member 33 is shaped to define a female contact face 43 remote from the tail portion 35 of the first member 33, the face being centrally indented to define a curved trough or channel 45 having the curve lying in a plane containing the tail portion 35 of the first member 33.

FIG. 10 shows a section through the trough 45 of the head 37, taken along a lateral plane containing the tail 35. In other words, the FIG. 10 section is taken in the upper portion of the face 43 of the head 37. As the trough extends downwardly around the curve of the face 43, it deepens as can be seen in the FIG. 11 section, which is a section taken radially of the curved face 43 at a lower point, corresponding to the section 6—6 in FIG. 5.

The head 41 of the second member 48 defines a male contact face 48 remote from the tail portion 40 of the second member 38, the male contact base 48 being centrally protuberant to define a curved ridge 50, the curve of the ridge 50 lying in a plane containing the tail portion 40 of the second member 38. A sectional view of the ridge 50 is visible in both FIG. 10 and 11.

As can be seen in the latter two figures, the trough 45 and the ridge 50 are shaped such that, when the members are in face-to-face contact in a first angular position corresponding to FIG. 11 (and comparable to the relationship shown in FIG. 5), the ridge 50 and the trough 45 are substantially complementary with each other in the area of contact, such that lateral articulation of the tail portions 35 and 40, in a plane normal to the planes of the ridge curve and the trough curve, is restrained; and when the two members are in face-to-face contact in a second angular position corresponding to FIG. 10 and also to the orientation shown in FIG. 8, the respective contacting areas of the ridge 50 and trough 45 are non-complementary, and such that the trough 45 allows the ridge 50 and its tail portion 35 to articulate laterally in the said plane normal to the ridge curve and trough curve planes.

Geometrically, the gradually varying shape of the base 43 of the head 37 may be thought of as consisting of two circular portions having different centres of curvature. The base of the trough 45 is circular but has a centre of curvature lying somewhat above the centre of curvature of the rounded convex shoulder portions 53 which run along and define between them the central concave trough 45. The centre of curvature of the trough 45 is also slightly displaced in the direction of the tail portion 45 of the first member 33.

The tail portions of both parts in both embodiments are of conventional construction, and include flutes or ribs extending radially which can be lodged and cemented into a suitably prepared end of the respective bone. Such preparation usually involves routing or cleaning of the central marrow portion of the bone, to provide a recess in which the tail portion of the respective member can be received.

I claim:

1. A joint replacement comprising:
   a first member having a head portion and an elongated tail portion, the latter adapted for insertion into one bone of a joint,
   a second member having a head portion and an elongated tail portion, the latter adapted for insertion into another bone of the joint,
   the head of said fist member defining a female contact face remote from the tail portion of the first member, said face being centrally indented to define a curved trough with the curve lying in a plane containing the tail portion of the first member,
   the head of said second member defining a male contact face remote from the tail portion of the second member, said male face being centrally protuberant to define a curved ridge with the curve lying in a plane containing the tail portion of the second member,
   the trough and the ridge being so shaped that, when the two members are in face-to-face contact in a first angular portion, the ridge and trough are substantially complementary with each other in the area of contact, such that lateral articulation of the tail portions in a plane normal to the planes of the ridge and trough is restrained, and when the two members are in face-to-face contact in a second angular position the respective contacting areas of the ridge and trough are non-complementary and such that the trough allows the ridge and its tail portion to articulate laterally in said plane normal to the ridge and trough planes, the profile of the trough being substantially constant, and the profile of the ridge changing smoothly around the curve thereof from more protuberant to less protuberant.

2. The invention claimed in claim 1, in which the profile of the trough is that of an obtuse angled V, and in which the profile of the ridge is V-shaped throughout but merges smoothly from a V complementary with the trough to a V of less vertex angle than the trough.

3. The invention claimed in claim 1 or claim 3, in which the ridge of the second member is longer around its curve than is the trough of the first member.

4. A joint replacement comprising:
   a first member having a head portion and an elongated tail portion, the latter adapted for insertion into one bone of a joint,
   a second member having a head portion and an elongated tail portion, the latter adapted for insertion into another bone of the joint,
   the head of said first member defining a female contact face remote from the tail portion of the first member, said face being centrally indented to define a curved trough with the curve lying in a plane containing the tail portion of the first member,
   the head of said second member defining a male contact face remote from the tail portion of the second member, said male face being centrally protuberant to define a curved ridge with the curve lying in a plane containing the tail portion of the second member,
   the trough and the ridge being so shaped that, when the two members are in face-to-face contact in a first angular portion, the ridge and trough are substantially complementary with each other in the area of contact, such that lateral articulation of the tail portions in a plane normal to the planes of the ridge and trough is restrained, and when the two members are in face-to-face contact in a second angular position the respective contacting areas of the ridge and trough are non-complementary and such that the trough allows the ridge and its tail portion to articulate laterally in said plane normal to the ridge and trough planes,
   the profile of the trough including a rounded concave central portion and rounded convex shoulder portions running along and defining between them the central portion, the profile of the ridge including a rounded convex central portion and rounded concave shoulder portions running alongside the central portion; the distance through which the concave central portion of the trough is recessed with respect to said rounded convex shoulder portions varying smoothly from a minimum value to a maximum vale, the profiles of the trough and ridge being complementary where said distance is at its maximum value, the two members being free to articulate laterally when the first member is being contacted where said distance is at its minimum value.

5. A joint replacement comprising:
   a first member having a head portion and an elongated tail portion, the latter adapted for insertion into one bone of a joint,
   a second member having a head portion and an elongated tail portion, the latter adapted for insertion into another bone of the joint,
   the head of said first member defining a female contact face remote from the tail portion of the first member, said face being centrally indented to define a curved trough with the curve lying in a plane containing the tail portion of the first member,
   the head of said second member defining a male contact face remote from the tail portion of the second member, said male face being centrally protuberant to define a curved ridge with the curve lying in a plane containing the tail portion of the second member,
   the trough and the ridge being so shaped that, when the two members are in face-to-face contact in a first angular portion, the ridge and trough are substantially complementary with each other in the area of contact, such that lateral articulation of the tail portions in a plane normal to the planes of the ridge and trough is restrained, and when the two members are in face-to-face contact in a second angular position the respective contacting areas of the ridge and trough are non-complementary and such that the trough allows the ridge and its tail portion to articulate laterally in said plane normal to the ridge and trough planes,
   the profile of the ridge being substantially constant, the profile of the trough changing smoothly around the curve thereof from more recessed to less recessed.

* * * * *